United States Patent [19]

Martin et al.

[11] 4,340,727
[45] Jul. 20, 1982

[54] 1,2-MODIFIED FORTIMICINS A AND B, INTERMEDIATES THEREFOR AND METHOD FOR THEIR MANUFACTURE

[75] Inventors: Jerry R. Martin; John S. Tadanier, both of Waukegan; Paulette Johnson, Zion, all of Ill.

[73] Assignee: Abbott Laboratories, North Chicago, Ill.

[21] Appl. No.: 201,651

[22] Filed: Oct. 28, 1980

Related U.S. Application Data

[63] Continuation of Ser. No. 79,135, Sep. 26, 1979, Pat. No. 4,273,925.

[51] Int. Cl.$^3$ ............................................ C07H 15/22
[52] U.S. Cl. .................................... 536/16.1; 424/180
[58] Field of Search ........................... 536/17 B, 17 R

[56] References Cited

U.S. PATENT DOCUMENTS

| | | | |
|---|---|---|---|
| 4,091,032 | 5/1978 | Tadanier et al. | 536/17 B |
| 4,218,442 | 8/1980 | McAlpine et al. | 536/17 B |
| 4,220,755 | 9/1980 | Sato et al. | 536/17 B |

*Primary Examiner*—Johnnie R. Brown
*Attorney, Agent, or Firm*—Joyce R. Niblack; Gildo E. Fato; Dennis K. Shelton

[57] ABSTRACT

A 1,2-modified fortimicin A or B represented by the formulae I, II and III:

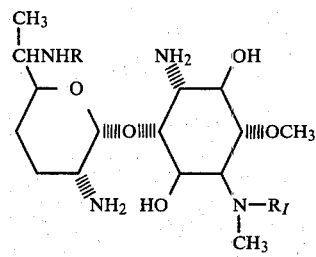

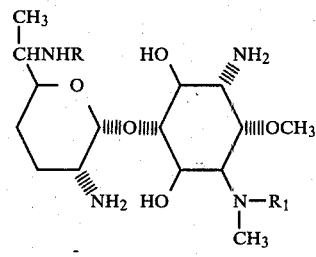

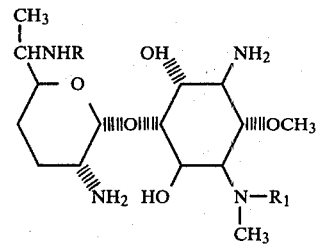

wherein R is hydrogen or loweralkyl; and $R_1$ is selected from the group consisting of hydrogen, loweralkyl, aminoloweralkyl, diaminoloweralkyl, N-loweralkylaminoloweralkyl, N,N-diloweralkylaminoloweralkyl, hydroxyloweralkyl, amino hydroxyloweralkyl, N-loweralkylaminohydroxyloweralkyl, N-N-diloweralkylaminohydroxyloweralkyl, acyl, aminoacyl, hydroxy-substituted aminoacyl, diaminoacyl, hydroxyacyl, hydroxy-substituted diaminoacyl, N-loweralkylaminoacyl, N, N-diloweralkylaminoacyl, hydroxysubstituted-N-loweralkylaminoacyl and hydroxy-substituted-N, N-diloweralkylaminoacyl, and the pharmaceutically acceptable salts thereof. The compounds are broad spectrum antibiotics.

10 Claims, No Drawings

1,2-MODIFIED FORTIMICINS A AND B, INTERMEDIATES THEREFOR AND METHOD FOR THEIR MANUFACTURE

This is a continuation, of application Ser. No. 79,135 filed Sept. 26, 1979, now U.S. Pat. No. 4,273,925.

BACKGROUND OF THE INVENTION

Aminoglycoside antibiotics are a valuable class of therapeutic agents which include the gentamicins, neomycins, streptomicins, kanamycins and the more recently discovered fortimicins. It has been found that the antibacterial and pharmacological properties of many naturally produced aminoglycoside antibiotics can be altered by structural modifications to provide derivatives which are either less toxic than the parent antibiotic or with advantageously altered anti-bacterial spectrums which either have increased intrinsic activity against one or more organisms or increased activity against resistant strains.

Further, historically, once an aminoglycoside antibiotic has been in clinical use for a period of time, resistant microorganisms develop. In many cases, the resistance is R-factor mediated and is attributed to the ability of the bacteria to enzymatically modify the amino or hydroxyl groups of the aminoglycoside antibiotics. Thus, there is also a need for new entities which can be held in reserve to combat strains which have become resistant to treatment by the clinically used antibiotics.

The fortimicins are a relatively new class of aminoglycoside antibiotics. Fortimicin A is disclosed in U.S. Pat. No. 3,976,768 and fortimicin B in U.S. Pat. No. 3,931,400. Chemical modification of the parent fortimicins have been found to either increase the intrinsic activity against one or more microorganisms, reduce the toxicity or provide therapeutic agents which, while having about the same, or perhaps somewhat weaker activity than the parent compounds or other derivatives, nevertheless are useful as reserve antibiotics in the event resistant strains develop after a period of clinical use of one or more of the fortimicins.

The derivatives provided to date include the 4-N-acyl and alkyl derivatives of fortimicin B (U.S. Pat. No. 4,091,032); 3-O-demethylfortimicins A and B and derivatives (U.S. Pat. No. 4,124,756), 2-deoxyfortimicin B (U.S. Pat. No. 4,169,198); 2-deoxyfortimicin A and 4-N-fortimicin B derivatives (U.S. Pat. No. 4,169,198), 1-epi-derivatives of fortimicins A and B (U.S. Pat. Nos. 4,218,441 and 4,218,442), and 2-epi-derivatives of fortimicins A and B (U.S. Ser. No. 79,130, filed Sept. 26, 1979, a continuation-in-part of U.S. Ser. No. 25,236 filed Mar. 29, 1979 now abandoned).

While a number of fortimicin derivatives have been made to date, including the above mentioned ones, and valuable therapeutic agents identified, the search continues for new fortimicin derivatives which exhibit either a broader spectrum, less ototoxicity, oral activity or which can be held in reserve and used to treat infections caused by organisms which have become resistant to therapy with other fortimicins.

The present invention provides a new class of fortimicin derivatives.

SUMMARY OF THE INVENTION

The present invention provides 1,2-modified fortimicins A and B which are useful as broad spectrum antibiotics in treating infections caused by susceptible strains of *Staphylococcus aureus, Enterobacter aerogenes, Escherichia coli, Klebsiella pneumoniae, Providencia stuartii, Pseudomonas aeruginosa, Salmonella typhurium, Serratia marcescens, Shigella sonnei, Proteus rettgeri, Proteus vulgaris* and *Proteus mirabilis*.

Intermediates useful in making the novel compounds as well as pharmaceutical compositions and methods of manufacture are also provided.

DETAILED DESCRIPTION OF PREFERRED EMBODIMENTS

The 1,2-modified fortimicins of this invention are represented by Formulae I, II and III.

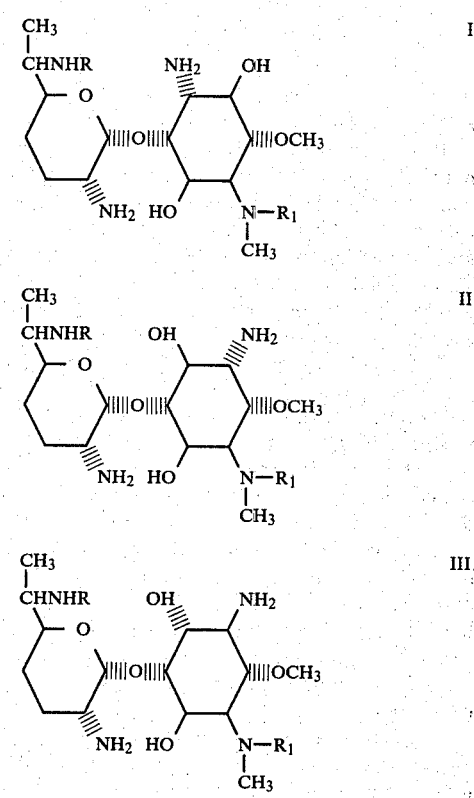

wherein R is hydrogen or loweralkyl; and $R_1$ is selected from the group consisting of hydrogen, loweralkyl, aminoloweralkyl, diaminoloweralkyl, N-loweralkylaminoloweralkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, acyl, aminoacyl, hydroxy-substituted aminoacyl, diaminoacyl, hydroxyacyl, hydroxy-substituted diaminoacyl, N-loweralkylaminoacyl, N,N-diloweralkylaminoacyl, hydroxy-substituted-N-loweralkylaminoacyl and hydroxy-substituted-N,N-dilower-alkylaminoacyl, and the pharmaceutically acceptable salts thereof.

Compounds of Formula I are 1,2-di-epi-fortimicin A and B and derivatives.

Compounds of Formula II are 2-amino-1-deamino-2-deoxy-1-hydroxyfortimicins A and B and derivatives.

Compounds of Formula III are 2-epi-amino-1-deamino-2-deoxy-1-epi-hydroxyfortimicins A and B and derivatives.

When $R_1$ is hydrogen, the compounds, fortimicins B, are useful as intermediates in the preparation of the corresponding fortimicins A ($R_1$=glycyl) and 4-N-fortimicin B derivatives which are useful as antibiotics.

The term "loweralkyl", as used herein, refers to straight or branched chain alkyl radicals having from 1 to 7 carbon atoms, including, but not limited to methyl, ethyl, n-propyl, iso-propyl, n-butyl, sec-butyl, tert-butyl, n-pentyl, 2-methylbutyl, 2,2-dimethylpropyl, n-hexyl, 2,2-dimethylbutyl, 1-methylpentyl, 3-methylpentyl, n-heptyl and the like.

The term "acyl", as used herein in the definition of $R_1$ in the specification and claims refers to acyl groups represented by the Formula

wherein $R_2$ is loweralkyl, i.e., acetyl, propionyl, butyryl, valeryl and the like.

The terms "aminoacyl" et seq. for $R_2$ include the naturally occurring amino acids such as glycyl, valyl, β-alanyl, alanyl, sarcosyl, leucyl, isoleucyl, prolyl, seryl, and the like as well as groups such as 2-hydroxy-4-aminobutyryl, 2-hydroxy-4-aminobutyl, etc. The amino acids residues included in the above terms can be in the L- or D- configurations or a mixture thereof, with the exception of course of glycyl and β-alanyl.

The term "pharmaceutically acceptable salts", as used herein, refers to the non-toxic acid addition salts of the compounds of this invention which can be prepared in situ during the final isolation and purification or by separately reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salts of this invention can be per-N-salts.

The Compounds of Formulae I, II and III are useful as broad spectrum antibiotics when administered parenterally to a patient suffering from an infection caused by a susceptible strain of bacilli in dosages of from 10 to 100 mg/kg of body weight daily, based on lean body weight as is good medical practice with the aminoglycoside antibiotics, and preferably from about 15 to about 30 mg/kg of body weight daily. The compounds are preferably administered in divided doses, i.e., three to four times daily and can be administered by intravenous, intramuscular, intraperitoneal, or subcutaneous routes of administration for systemic activity and orally to sterilize the intestinal tract. The antibiotics of this invention can also be administered in suppository form.

The antibiotics of Formula I, II and III can be used as described above in the treatment of infections caused by susceptible strains of organisms such as *Staphylococcus aureus, Enterobacter aerogenes, Escherichia coli, Klebsiella pneumoniae, Providencia stuartii, Pseudomonas aeruginosa, Salmonella typhimurium, Shigella sonnei, Proteus rettgeri, Proteus vulgaris* and *Proteus mirabilis* and *Serratia mercescens*.

The term "susceptible strains" refers to strains of bacilli which have been demonstrated to be sensitive to a particular antibiotic in a standard in vitro sensitivity test and thus in vitro activity has been established for a particular antibiotic against a specific strain of a specific organism.

The compounds of Formulae I, II and III can also be incorporated into scrub solutions for sterilizing surfaces such as laboratory benchtops, operating room surfaces and the like.

The preparation of the $C_1$–$C_2$ modified fortimicins of this invention are set forth in detail in the examples. Generally speaking, Fortimicin B, having all primary amino groups protected by suitable amine-protecting group such as a monocyclicaryloxycarbonyl, i.e., benzyloxycarbonyl groups, and the $C_2$ hydroxyl group converted to a 2-O-methanesulfonyl ester, is treated with sodium cyanide to form a 2',6'-di-N-benzyloxycarbonyl-2-deoxy-1,2(R)-epiminofortimicin B-4,5-carbamate derivative which is readily converted to a 2',6'-di-N-benzyloxycarbonyl-1-deamino-2,3-anhydro-fortimicin B-4,5-carbamate derivative by treatment with sodium nitrite. The latter carbamate is then converted to a mixture of bromohydrins by treatment with bromoacetamide in the presence of perchloric acid. The mixture of bromohydrins on treatment with 1,5-diazabicyclo [5.4.0]-undecene 5 (DBU) gives a 2',6'-di-N-benzyloxycarbonyl-1-deamino-1,2(R)-epoxyfortimicin B-4,5-carbamate which in turn is treated with sodium azide to form a mixture of 2',6'-di-N-benzyloxycarbonyl-1-azido-1-deamino-1,2-di-epifortimicin B-4,5-carbamate and 2',6'-di-N-benzyloxycarbonyl-2-azido-1-deamino-2-deoxy-1-hydroxyfortimicin B-4,5-carbamate. Catalytic hydrogenation followed by basic hydrolysis of the carbamate function gives 1,2-di-epifortimicin B and 2-amino-1-deamino-2-deoxy-1-hydroxyfortimicin B.

The latter fortimicins are readily converted to the corresponding 4-N-acylfortimicins following the procedures of U.S. Pat. No. 4,091,032. Briefly, the primary amine groups can be blocked by treatment with a suitable acylating agent such as N-(benzyloxycarbonyloxy)succinimide. The secondary amine group is in turn acylated by an active carboxylic acid derivative to obtain a per-N-blocked $C_1$ and/or $C_2$ modified 4-N-acylfortimicin which is converted to the corresponding deprotected fortimicin by catalytic hydrogenation.

The 4-N-alkyl derivatives can be obtained by reduction of the $C_4$-amides with diborane.

6'-N-methylation can be effected by subjecting a compound of Formulae I, II or III to selective N-carbobenzyloxyation with one mole of an active ester of benzylcarbonate, followed by subsequent reduction with a suitable metal hydride such as lithium aluminum hydride as taught in commonly assigned U.S. Pat. No. 4,205,070.

2-epi-Amino-1-deamino-2-deoxy-1-epi-hydroxyfortimicin B can be obtained by treatment of a 2',6'-di-N-benzyloxycarbonyl-1-deamino-2,3-anhydrofortimicin B-4,5-carbamate with m-chloroperoxybenzoic acid which results in 2',6'-di-N-benzyloxycarbonyl-1-deamino-1,2(S)-epoxyfortimicin B-4,5-carbamate. Subsequent treatment with sodium azide gives a mixture of 2',6'-di-N-benzyloxycarbonyl-2-epi-azido-1-deamino-2-deoxy-1-epi-hydroxyfortimicin B-4,5-carbamate and 2',6'-di-N-benzyloxycarbonyl-1-azido-1-deaminofortimicin B-4,5-carbamate. Catalytic reduction followed by removal of the carbamate function gives 2-epi-amino-1-deamino-2-deoxy-1-epi-hydroxyfortimicin B and fortimicin B.

The present invention also provides intermediates, in addition to the compounds of Formulae I, II and III wherein $R_1$ is hydrogen, represented by Formulae:

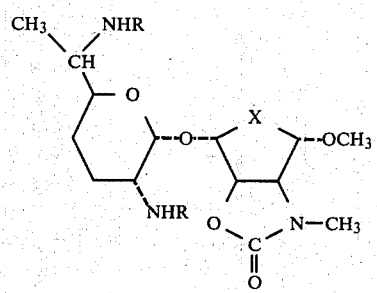

wherein R is hydrogen or monocyclicaryloxycarbonyl, and X is selected from a group consisting of

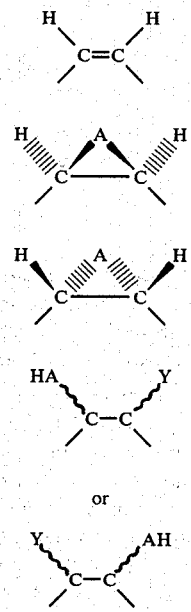

wherein A is a divalent hetero atom such as oxygen or sulfur or a monosubstituted trivalent hetero atom such as NH, and Y is a nucleophile such as azide, bromide, or amine.

EXAMPLE 1

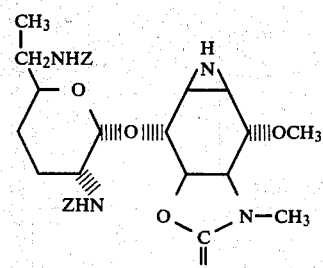

2',6'-Di-N-benzyloxycarbonyl-2-deoxy-1,2(R)-epiminofortimicin B-4,5-carbamate

A stirring suspension prepared from 3.134 g of 1,2',6'-tri-N-benzyloxycarbonyl-2-O-methanesulfonylfortimicin B, 3.134 g of sodium cyanide, and 165 ml of dimethylformamide is heated at 93° C. for 20 hours. The reaction mixture is diluted with water and extracted repeatedly with chloroform. The chloroform extract is washed with water, dried over magnesium sulfate, and evaporated. Residual dimethylformamide is removed by repeated co-distillation with toluene to leave a residue which is chromatographed on a column (3.1×80 cm) of silica gel eluted with a mixture of benzene-methanol-95% ethanol-concentrated ammonium hydroride [23.5:1.4:2.0:0.2 (v/v)]. Fractions containing the major component are concentrated to dryness to give a residue which is crystallized from methanol-water to give 0.819 g of 2',6'-di-N-benzyloxycarbonyl-2-deoxy-1,2(R)-epiminofortimicin B-4,5-carbamate: m.p. 201°–205° C., recrystallizes at 203° C. and remelts at 218°–219° C.; $[\alpha]_D^{25}+39.8°$ (c 0.94, chloroform); I.R. (CDCl$_3$) 3440, 1747, 1708 and 1500 cm$^{-1}$; PMR (CDCl$_3$) $\alpha$1.16 (d, C$_{6'}$ -CH$_3$, J$_{6',7'}$=7.0 Hz). 2.83 (s, C$_4$-NCH$_3$), 3.38 (s, C$_3$-OCH$_3$), 4.95 (d, H$_1$, J$_{1',2'}$=3.5 Hz), 7.33 (m, Cbz-aromatic).

Anal. Calcd. for C$_{32}$H$_{40}$N$_4$O$_9$: C, 61.53; H, 6.45; N, 8.97. Found: C, 61.35; H, 6.55; N, 8.94.

EXAMPLE 2

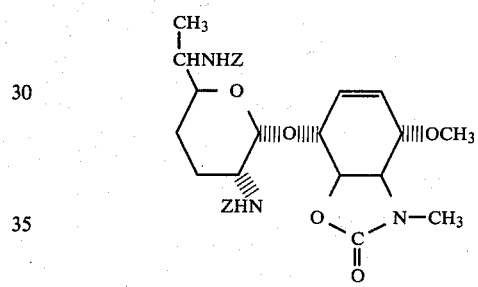

2',6'-Di-N-benzyloxycarbonyl-1-deamino-1,2-anhydrofortimicin B-4,5-carbamate

A stirring solution prepared from 10.5 g of 2',6'-di-N-benzyloxycarbonyl-2-deoxy-1,2(R)-epiminofortimicin B-4,5-carbamate and 487 ml of glacial acetic acid is treated dropwise with 6.75 g of sodium nitrite in 445 ml of water. The reaction mixture is stirred for 0.5 hour and then adjusted to pH 9.0 with sodium hydroxide. The product is isolated by chloroform extraction to give 9.583 g of 2',6'-di-N-benzyloxycarbonyl-1-deamino-1,2-anhydrofortimicin B-4,5-carbamate: I.R. (CDCl$_3$) 1740,1700 and 1445 cm$^{-1}$; P.M.R. (CDCl$_3$) δ1.16 (d, C$_{6'}$-CH$_3$, J$_{6',7'}$=7.0 Hz), 2.94 (s, C$_4$-NCH$_3$), 3.43 (s, C$_3$-OCH$_3$), 7.35 (Cbz-aromatic).

EXAMPLE 3

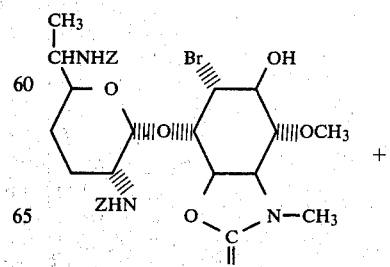

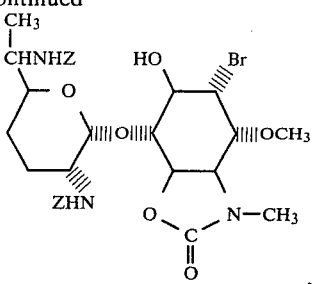

2',6'-Di-N-benzyloxycarbonyl-1-deamino-1,2-di-epi-2-bromofortimicin B-4,5-carbamate and
2',6'-Di-N-benzyloxycarbonyl-1-deamino-2-deoxy-1-hydroxy-2-bromofortimicin B-4,5-carbamate A stirring solution of 9.783 g of 2',6'-di-N-benzyloxycarbonyl-1-deamino-1,2-anhydrofortimicin B-4,5-carbamate, 118 ml of peroxide-free dioxane and 3.94 ml of perchloric acid, prepared by adding 3.5 ml of 60% perchloric acid to 46 ml of water, is treated with 4.2 g of freshly recrystallized bromoacetamide. After stirring for 3 hours, the reaction mixture is diluted with water and repeatedly partitioned with chloroform. The combined chloroform extract is washed with equal volumes of 5% sodium iodide, 5% sodium thiosulfate, 5% sodium carbonate and water. Evaporation of the chloroform under reduced pressure gives 9.762 g of a crude mixture of 1,2-di-epi-2-bromofortimicin B-4,5-carbamate and 2',6'-di-N-benzyloxycarbonyl-1-deamino-2-deoxy-1-hydroxy-2-bromofortimicin B-4,5-carbamate: I.R. (CDCl$_3$) 1504, 1710 and 1736 cm$^{-1}$.

EXAMPLE 4

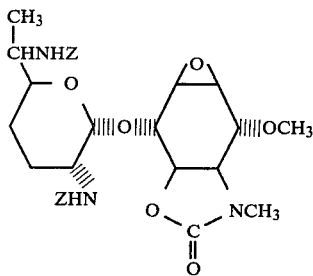

2',6'-Di-N-benzyloxycarbonyl-1-deamino-1,2(R)-epoxyfortimicin B-4,5-carbamate

A solution prepared from 14.76 g of the crude mixture of Example 3, 295 ml of benzene and 21 ml of 1,5-diazabicyclo [5.4.0] undecene 5 (DBU) is stirred at room temperature for 2 hours. The reaction is stirred for an additional 0.5 hour, followed by the addition of 400 ml of benzene and 400 ml of water. After shaking, the benzene layer is separated and the aqueous portion is extracted with benzene. The combined benzene extracts are washed with 5% aqueous sodium bicarbonate solution and then with water. Evaporation under reduced pressure leaves a solid which is chromatographed on a column of silica gel with a solvent system consisting of ethylacetate-hexane [3:1 (v/v)]. Fractions containing only the major component are evaporated to dryness to give 2',6'-di-N-benzyloxycarbonyl-1-deamino-1,2(R)-epoxyfortimicin B-4,5-carbamate: IR (CDCl$_3$) 1506, 1711, and 1752 cm$^{-1}$; P.M.R. (CDCl$_3$) $\delta$1.22 d, (C$_{6'}$-CH$_3$, J$_{6'7'}$=6.5 Hz.), 2.86 (s, C$_4$-NCH$_3$), 3.45 (s, C$_3$-OCH$_3$), 7.34 (m, Cbz-aromatic).

EXAMPLE 5

2',6'-Di-N-benzyloxycarbonyl-1-azido-1-deamino-1,2-di-epi-fortimicin B-4,5-carbamate and
2',6'-Di-N-benzyloxycarbonyl-2-azido-1-deamino-2-deoxy-1-hydroxyfortimicin B-4,5-carbamate A solution prepared from 5.574 g of 2',6'-di-N-benzyloxycarbonyl-1-deamino-1,2(R)-epoxyfortimicin B-4,5-carbamate, 100 ml of dry dimethylformamide, 5.576 g of sodium azide and 5.576 g of boric acid is refluxed for 2.5 hours. The reaction mixture is added to 1100 ml of 5% aqueous sodium bicarbonate solution and repeatedly extracted with portions of chloroform. The combined chloroform extracts are washed with water and evaporated under reduced pressure. Residual dimethylformamide is removed by repeated co-distillation with toluene to give 5.82 g of solid. The solid is chromatographed on a column of silica gel with a solvent system consisting of ethyl acetate-hexane [3:1 (v/v)]. Fractions containing the major components are taken to dryness to give 4.825 g of a mixture of 2',6'-di-N-benzyloxycarbonyl-1-azido-1-deamino-1,2-di-epi-fortimicin B-4,5-carbamate and 2',6'-di-N-benzyloxycarbonyl-2-azido-1-deamino-2-deoxy-1-hydroxyfortimicin B-4,5-carbamate: I.R. (CDCl$_3$) 2110, 1755, 1710 and 1053 cm$^{-1}$.

EXAMPLE 6

-continued

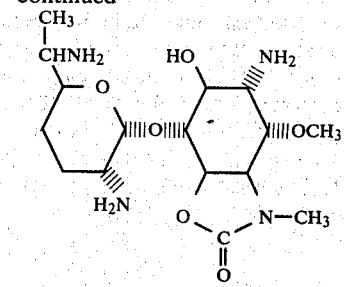

1,2-Di-epi-fortimicin B-4,5-carbamate and
2-amino-1-deamino-2-deoxy-1-hydroxyfortimicin
B-4,5-carbamate A solution prepared from 2.31 g of the mixture of 2′,6′-di-N-benzyloxycarbonyl-1-azido-1-deamino-1,2-di-epi-fortimicin B-4,5-carbamate and 2′,6′-di-N-benzyloxycarbonyl-2-azido-1-deamino-2-deoxy-1-hydroxyfortimicin B-4,5-carbamate prepared in Example 5 and 250 ml of 0.2 N hydrochloric acid in methanol is hydrogenated over 2.31 g of 5% palladium on carbon for 4 hours under 3 atmospheres of hydrogen. The catalyst is removed by filtration and the filtrate is evaporated to dryness under reduced pressure. Excess hydrochloric acid is removed by repeated co-distillation with methanol to give 1.635 g of a mixture 1,2-di-epi-fortimicin B-4,5-carbamate and 2-amino-1-deamino-2-deoxy-1-hydroxyfortimicin B-4,5-carbamate isolated as the per hydrochloride salts: I.R. (KBr) 1497, 1605 and 1736 cm$^{-1}$.

EXAMPLE 7

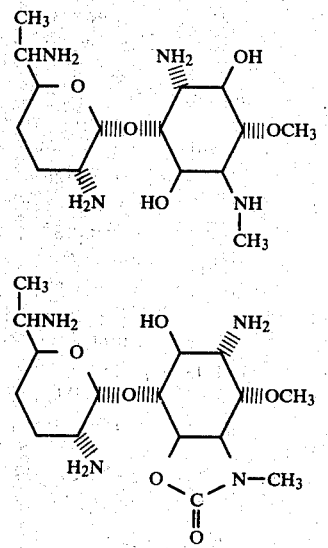

1,2-Di-epi-fortimicin B and
2-Amino-1-deamino-2-deoxy-1-hydroxyfortimicin B

A stirring suspension prepared from 1.657 g of a mixture of 1,2-di-epi-fortimicin B-4,5-carbamate and 2-amino-1-deamino-2-deoxy-1-hydroxyfortimicin B-4,5-carbamate prepared by the procedure of Example 6, 265 ml of water and 49.3 ml of barium hydroxide is heated at 70° C. for 18 hours. After cooling, carbon dioxide gas is passed through the reaction mixture. The resulting barium carbonate is removed by centrifugation. The pellet is washed with water and the above procedure is repeated twice more. The combined supernaturants and pellet washings are taken to dryness under reduced pressure to give 1.248 g of a mixture of 1,2-di-epi-fortimicin B and 2-amino-1-deamino-2-deoxy-1-hydroxyfortimicin B.

A sample (2.437 g) of a mixture prepared as above is chromatographed on a column (2.2×39 cm) of a cation exchange resin, e.g., Bio Rex 70, 100–200 mesh, NH$_4$+ form, manufactured by BioRad Laboratories, and eluted with a gradient of water to 1 N ammonium hydroxide. Fractions containing only the first component eluted are taken to dryness under reduced pressure to give a solid. To decompose carbonates, the solid is treated with 25 ml of 0.2 N hydrochloric acid in methanol. The methanol is evaporated to dryness and excess hydrochloric acid is removed by repeated co-distillation with methanol to give 0.555 g of 1,2-di-epi-fortimicin B hydrochloride. 1,2-Di-epi-fortimicin free base is prepared from the hydrochloride salt by passing a water solution of the salt through a column of an anion exchange resin, e.g., AG ® 2-X8, 100–200 mesh, hydroxyl form, manufactured by Bio Rad Laboratories, sufficient to remove chloride ion. The elutes are taken to dryness to give 1,2-di-epi-fortimicin B: I.R. (KBr) 1443 and 1578 cm$^{-1}$; P.M.R. (D$_2$O) δ1.55 (d,C$_6$-CH$_3$), J$_{6',7'}$=7.0 Hz), 2.84 (s, C$_4$-NCH$_3$), 4.04 (s, C$_3$-OCH$_3$), 5.36 (d, H$_{1'}$, J$_{1',2'}$=3.0 Hz); mass spectrum, m/e 349.2428 (M+H)+, calcd. for C$_{15}$H$_{33}$N$_4$O$_5$ 349.2451.

Continued elution gives fractions which are taken to dryness under reduced pressure. The resulting solid is treated with 0.2 N hydrochloric acid in methanol. The methanol is evaporated to dryness and excess hydrochloric acid is removed by repeated co-distillation with methanol to give 0.555 g of 2-amino-1-deamino-2-deoxy-1-hydroxyfortimicin B hydrochloride. 2-Amino-1-deamino-2-deoxy-1-hydroxyfortimicin B free base is prepared from the hydrochloride salt by passing a water solution of the salt through a column of an anion exchange resin, e.g., AG ® 2-X8, 100–200 mesh, hydroxyl form, manufactured by Bio Rad Laboratories, sufficient to remove chloride ion. The elutes are taken to dryness to give 2-amino-1-deamino-2-deoxy-1-hydroxyfortimicin B: I.R. (KBr) 1445 and 1585 cm$^{-1}$; P.M.R. (D$_2$O) δ 1.50 (d, C$_6$'-CH$_3$, J$_{6',7'}$=6.5 Hz), 2.85 (s, C$_4$-NCH$_3$) 3.92 (s, C$_3$-OCH$_3$), 5.55 (d, H$_{1'}$, J$_{1',2'}$=4.0 Hz); mass spectrum, meas. 349.2422 (M+H)+, calcd. for C$_{15}$H$_{33}$N$_4$O$_5$ 349.2451.

EXAMPLE 8

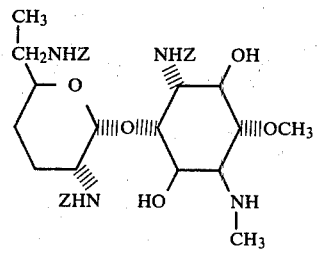

1,2′,6′-Tri-N-benzyloxycarbonyl-1,2-di-epi-fortimicin B

A stirring ice-bath cooled solution prepared from 0.252 g of 1,2-di-epi-fortimicin B free base in 3.8 ml of water and 7.6 ml of methanol is treated with 0.555 g of N-(benzyloxycarbonyloxy)succinimide. Stirring is continued in the cold for 3 hours and then at room temperature for 22 hours. Solvent is removed under reduced pressure to leave a syrup which is shaken with a mixture of chloroform and water. The chloroform layer is separated, washed with water, dried over magnesium sulfate, and evaporated to give 0.385 g of solid which is chromatographed on a column (1.5×75 cm) of silica gel prepared and eluted with a solvent system consisting of dichloroethane - 95% ethanol ammonium hydroxide [18:2:0.04 (v/v)]. Fractions containing the slowest moving component are taken to dryness under reduced pressure to give 0.155 g of 1,2',6'-tri-N-benzyloxycarbonyl-1,2-di-epi-fortimicin B: I.R. (CDCl$_3$) 1505 and 1705 cm$^{-1}$; P.M.R. (CDCl$_3$) δ2.42 (s, C$_4$-NCH$_3$), 3.58 (s, C$_3$-OCH$_3$).

EXAMPLE 9

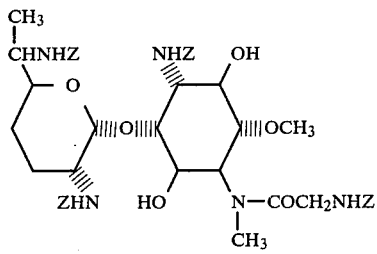

1,2',6',2''-Tetra-N-benzyloxycarbonyl-1,2-di-epi-fortimicin A

A stirring solution prepared from 0.155 g of 1,2',6'-tri-N-benzyloxycarbonyl-1,2-di-epi-fortimicin B in 2.7 ml of tetrahydrofuran is treated with 0.067 g of N-(benzyloxycarbonylglycyloxy) succinimide. Stirring is continued for 17 hours at room temperature. The tetrahydrofuran is evaporated under reduced pressure to leave a residue which is chromatographed on a column (1.2×70 cm) of silica gel using dichloroethane -95% ethanol-concentrated ammonium hydroxide [18:6:0.04 (v/v)] as the eluent to give 0.098 g of 1,2',6',2''-tetra-N-benzyloxycarbonyl-1,2-di-epi-fortimicin A: I.R. (CDCl$_3$) 1496, 1637 and 1697 cm$^{-1}$; P.M.R. (CDCl$_3$) δ 1.02 (d, C$_{6'}$-CH$_3$, J$_{6',7'}$=6.5 Hz), 2.88 (s, C$_4$-NCH$_3$), 3.46 (s, C$_3$-OCH$_3$), 7.31 (m, Cbz-aromatic).

Anal. Calcd for C$_{49}$H$_{59}$N$_5$O$_{14}$: C, 62.48; H, 6.31; N, 7.43. Found: C, 62.95; H, 6.83; N, 7.00.

EXAMPLE 10

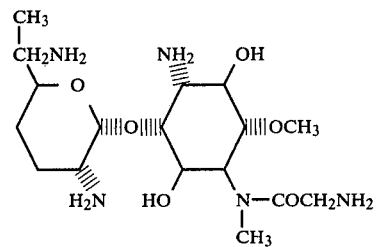

1,2-Di-epi-fortimicin A Tetrahydrochloride

A solution prepared from 0.098 g of 1,2',6',2''-tetra-N-benzyloxycarbonyl-1,2-di-epi-fortimicin A and 9 ml of 0.2 N hydrochloric acid in methanol is hydrogenated over 0.10 g of 5% palladium on carbon for 4 hours under 3 atmospheres of hydrogen. The catalyst is collected on a filter and washed with methanol. The filtrate and washings are concentrated to dryness and the excess hydrochloric acid is removed by repeated co-distillation with methanol under reduced pressure to give 0.057 g of 1,2-di-epi-fortimicin A isolated as the hydrochloride: I.R. (KBr) 3410, 2930, 1640, and 1490 cm$^{-1}$; P.M.R. (D$_2$O) δ 1.47 (d, C$_{6'}$-CH$_3$, J$_{6',7'}$=6.5 Hz), 3.51 (s, C$_4$-NCH$_3$), 3.83 (s, C$_3$-OCH$_3$), 5.31 (d, H$_{1'}$, J$_{1'2'}$=3.0 Hz) mass spectrum, meas. 405.2584, calcd. for C$_{17}$H$_{35}$N$_5$O$_6$ 405.2587.

EXAMPLE 11

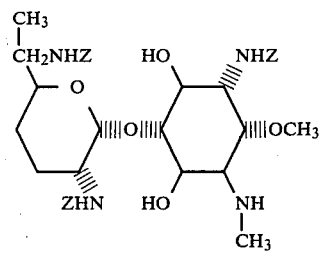

2,2',6'-Tri-N-benzyloxycarbonyl-2-amino-1-deamino-2-deoxy-1-hydroxyfortimicin B

A stirring, ice-bath cooled solution prepared from 0.358 g of 2-amino-1-deamino-2-deoxy-1-hydroxyfortimicin B free base, 5.4 ml of water and 10.8 ml of methanol is treated with 0.784 g of N-(benzyloxycarbonyloxy)succinimide. Stirring is continued in the cold for 3 hours and then at room temperature for 20 hours. Evaporation of the solvent gives a syrup which is partitioned between chloroform and water. The chloroform layer is washed with water and dried over magnesium sulfate. Evaporation of the chloroform under reduced pressure gives 0.578 g of residue. The residue is chromatographed on a column of silica gel prepared and eluted with a solvent system consisting of dichloroethane-95% ethanol-concentrated ammonium hydroxide [18:6:0.04 (v/v/v)]. Fractions containing the major product are taken to dryness and the resulting solid is rechromatographed on a column (1.7×75 cm) of Sephadex LH-20 (manufactured by Pharmacia Fine Chemicals, Inc.) using 95% ethanol as the eluent. Fractions containing only the major component are taken to dryness under reduced pressure to give 0.414 g of 2,2',6'-tri-N-benzyloxycarbonyl-2-amino-1-deamino-2-deoxy-1-hydroxyfortimicin B: I.R. (CDCl$_3$) 3438, 1702 and 1502 cm$^{-1}$; P.M.R. (CDCl$_3$) δ 1.14 (d, C$_6$, —CH$_3$, J$_{6',7'}$=6.5 Hz), 2.39 (s, C$_4$-NCH$_3$), 3.34 (s, C$_3$-OCH$_3$), 4.94 (d, H$_{1'}$, J$_{1',2'}$=3.7 Hz).

Anal. Calcd. for C$_{39}$H$_{50}$N$_4$O$_7$: C, 62.39; H, 6.71; N, 7.46. Found: C, 62.14; H, 6.88; N, 7.41.

EXAMPLE 12

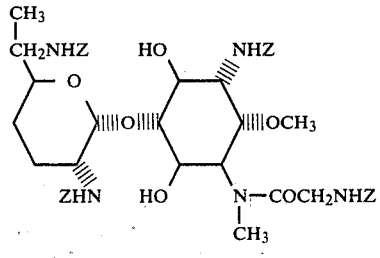

2,2′,6′,2″-Tetra-N-benzyloxycarbonyl-2-amino-1-deamino-2-deoxy-1-hydroxyfortimicin A A solution prepared from 0.177 g of 2,2′,6′-tri-N-benzyloxycarbonyl-2-amino-1-deamino-2-deoxy-1-hydroxyfortimicin B, 3.7 ml of tetrahydrofuran dried over molecular sieves, and 0.075 g of N-(benzyloxycarbonylglycyloxy) succinimide is stirred at room temperature for 21 hours. The tetrahydrofuran is evaporated under reduced pressure and the residue is chromatographed on a column (1.6×60 cm) of silica gel. Elution with a solvent system consisting of methylene chloride-methanol-concentrated ammonium hydroxide [96:3.5:0.05 (v/v)] gives homogeneous fractions containing the major component which are taken to dryness under reduced pressure to give 0.087 g of 2,2′,6′,2″-tetra-N-benzyloxycarbonyl-2-amino-1-deamino-2-deoxy-1-hydroxyfortimicin A: I.R. (CDCl$_3$) 1707, 1636 and 1505 cm$^{-1}$; P.M.R. (CDCl$_3$) δ 1.04 (unresolved doublet, C$_6$-CH$_3$), 2.92 (S, C$_4$-NCH$_3$), 3.34 (s, C$_3$-OCH$_3$), 7.28 (m, Cb$_2$-aromatic).

Anal. Calcd. for C$_{49}$H$_{59}$N$_5$O$_{14}$: C, 62.48; H, 6.31; N, 7.43. Found: C, 62.12; H, 6.57; N, 7.33.

EXAMPLE 13

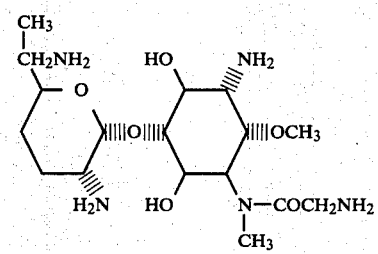

2-Amino-1-deamino-2-deoxy-1-hydroxyfortimicin A

A solution prepared from 0.087 g of 2,2′,6′,2″-tetra-N-benzyloxycarbonyl-2-amino-1-deamino-2-deoxy-1-hydroxyfortimicin A and 7.5 ml of 0.2 N hydrochloric acid in methanol is hydrogenated in the presence of 0.086 g of 5% palladium on carbon for 4 hours under 3 atmospheres of hydrogen. The catalyst is collected on a filter and washed with methanol. The filtrate and washings are concentrated to dryness under reduced pressure. Excess hydrochloric acid is removed by repeated co-distillation with methanol to give 0.063 g of 2-amino-1-deamino-2-deoxy-1-hydroxyfortimicin A isolated as the tetrahydrochloride: I.R. (KBr) 1645, 1590 and 1490 cm$^{-1}$; P.M.R. (D$_2$O) δ 1.79 (d, C$_6$-CH$_3$, J$_{6',7'}$=7.0 Hz), 3.59 (s, C$_4$-NCH$_3$), 3.87 (s, C$_3$-OCH$_3$), 5.87 (d, H$_1$, J$_{1',2'}$=3.5 Hz); mass spectrum, meas. 405.2576, calcd. for C$_{17}$H$_{35}$N$_5$O$_6$ 405.2587.

EXAMPLE 14

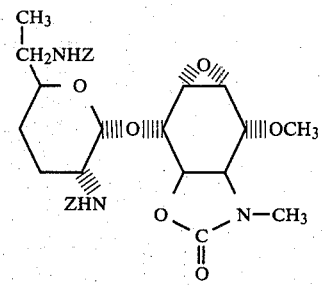

2′,6′-Di-N-benzyloxycarbonyl-1-deamino-1,2(δ)-epoxyfortimicin B-4,5-carbamate A stirring solution of 0.288 g of 2′,6′-di-N-benzyloxycarbonyl-1-deamino-2,3-anhydrofortimicin B-4,5-carbamate in 6 ml of methylene chloride is treated dropwise by the addition of 0.490 g on m-chloroperoxybenzoic acid in 8 ml of methylene chloride. The reaction is stirred at room temperature for 20 hours. After the addition of 55 ml of 5% aqueous sodium bicarbonate solution, chloroform extraction gives 0.531 g of residue. The residue is chromatographed on a column (1.6×71 cm) of silica gel eluted with a solvent system consisting of ethyl acetate-dichloroethane [9:1 (v/v)]. Evaporation of fractions containing the major component gives 0.143 g of 2′,6′-di-N-benzyloxycarbonyl-1-deamino-1,2(δ)-epoxyfortimicin B-4,5-carbamate: I.R. (CDCl$_3$) 1752, 1713 and 1503 cm$^{-1}$; P.M.R. (CDCl$_3$) δ 1.17 (d, C$_6$-CH$_3$, J$_{6',7'}$=7.0 Hz), 2.88 (s, C$_4$-NCH$_3$), 3.46 (s, C$_3$-OCH), 7.35 (m, Cbz-aromatic).

EXAMPLE 15

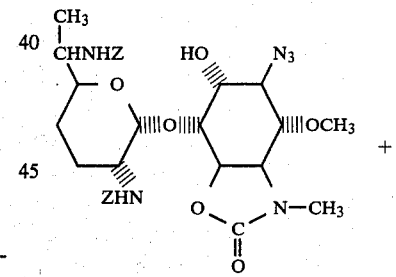

+

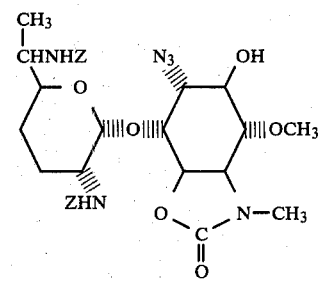

2′,6′-Di-N-benzyloxycarbonyl-2-epi-azido-1-deamino-2-deoxy-1-epi-aminofortimicin B-4,5-carbamate and 2′,6′-Di-N-benzyloxycarbonyl-1-azido-1-deaminofortimicin B-4,5-carbamate A solution prepared from 1.40 g of 2′,6′-di-N-benzyloxycarbonyl-1-deamino-1,2(δ)-epoxyfortimicin B-

4,5-carbamate, 1.397 g of boric acid, 1.397 g of sodium azide and 53 ml of dimethylformamide is refluxed for 2.5 hours. The reaction mixture is poured into 285 ml of aqueous 5% sodium bicarbonate solution and repeatedly extracted with chloroform. The chloroform extract is washed with water and evaporated. Residual dimethylformamide is removed by repeated co-distillation with toluene to leave a residue which is chromatographed on a column (2.2×71 cm) of silica gel using a solvent system consisting of ethyl acetate-dichloroethane (9:1 v/v). The first fractions eluted are taken to dryness to give 0.663 g of 2',6'-di-N-benzyloxycarbonyl-2-epi-azido-1-deamino-2-deoxy-1-epi-hydroxyfortimicin B-4,5-carbamate: I.R. (CDCl$_3$) 3438, 3345, 2940, 2110, 1755, 1712 and 1508 cm$^{-1}$; P.M.R. (CDCl$_3$) δ 1.16 (d, C$_6$'-CH$_3$, J$_{6',7'}$=7.0 Hz), 2.89 (s, C$_4$-NCH$_3$), 3.52 (s, C$_3$-OCH$_3$), 4.93 (d, H$_{1'}$, J$_{1',2'}$=4.0 Hz), 7.33 (m, Cbz-aromatic).

Anal. Calcd. for C$_{32}$H$_{40}$N$_6$O$_{10}$: C, 57.48; H, 6.03; N, 12.57. Found: C, 57.56; H, 6.30; N, 12.23.

Continued elution gives homogeneous fractions which are taken to dryness to give 0.530 g of 2',6'-di-N-benzyloxycarbonyl-1-azido-1-deaminofortimicin B-4,5-carbamate: I.R. (CDCl$_3$) 3555, 3435, 2935, 2112, 1762, 1710 and 1503 cm$^{-1}$; P.M.R. (CDCl$_3$) δ 1.19 (d, C$_6$'-CH$_3$, J$_{6',7'}$=6.0 Hz), 2.79 (s, C$_4$-NCH$_3$), 3.47 (s, C$_3$-OCH$_3$), 5.26 (d, H$_{1'}$, J$_{1',2'}$=4.0 Hz), 7.33 (m, Cbz-aromatic).

Anal. Calcd. for C$_{32}$H$_{40}$N$_6$O$_{10}$: C, 57.48; H, 6.03, N, 12.57. Found: C, 57.78, H, 6.45; N, 12.69.

EXAMPLE 16

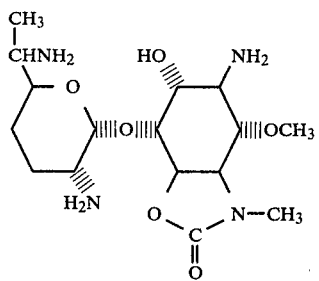

2-epi-Amino-1-deamino-2-deoxy-1-epi-hydroxyfortimicin B-4,5-carbamate trihydrochloride A solution prepared from 0.216 g of 2',6'-di-N-benzyloxycarbonyl-2-epi-azido-1-deamino-2-deoxy-1-epi-hydroxyfortimicin B-4,5-carbamate and 20 ml of 0.2 N hydrochloric acid in methanol is hydrogenated over 0.22 g of 5% palladium on carbon for 4 hours under 3 atmospheres of hydrogen. The catalyst is removed by filtration through a celite mat. The celite mat is washed with methanol and the filtrate and washings are evaporated to dryness under reduced pressure to leave a residue. To remove excess hydrochloric acid the residue is repeatedly co-distilled with methanol to give 0.169 g of 2-epi-amino-1-deamino-2-deoxy-1-epi-hydroxyfortimicin B-4,5-carbamate isolated as the trihydrochloride salt: I.R. (KBr) 3412, 2930, 1732, 1600 and 1493 cm$^{-1}$; P.M.R. (D$_2$O) δ 1.79 (d, C$_6$, —CH$_3$, J$_{6',7'}$=6.5 Hz), 3.48 (s, C$_4$-NCH$_3$), 4.05 (s, C$_3$-OCH$_3$), 5.82 (d, H$_{1'}$, J$_{1',2'}$=4.0 Hz); mass spectrum, meas. 374.2182, calcd. for C$_{16}$H$_{30}$N$_4$O$_6$ 374.2165.

EXAMPLE 17

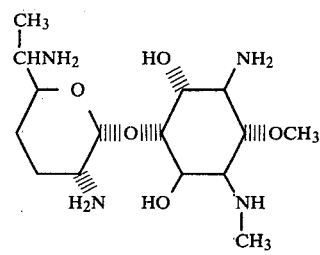

2-epi-Amino-1-deamino-2-deoxy-1-epi-hydroxyfortimicin B

A stirring mixture prepared from 0.123 g of 2-epi-amino-1-deamino-2-deoxy-1-epi-hydroxyfortimicin B-4,5-carbamate, 3.62 g of barium hydroxide and 19.6 ml of water is heated at 70° C. for 20 hours. The excess barium hydroxide is removed by filtration through a celite mat. Carbon dioxide gas is passed through the filtrate. The resulting barium carbonate is removed by centrifugation. The pellet is washed with water and the above process is repeated twice more. The combined supernatants and pellet washings are taken to dryness under reduced pressure to give 0.080 g of 2-epi-amino-1-deamino-2-deoxy-1-epi-hydroxyfortimicin B; I.R. (KBr) 1587 and 1440 cm$^{-1}$; P.M.R. (D$_2$O) δ 1.53 (d, C$_6$'-CH$_3$, J$_{6',7'}$=6.5 Hz), 2.86 (s, C$_4$-NCH$_3$), 4.03 (s, C$_3$-OCH$_3$), 5.38 (d, H$_{1'}$, J$_{1',2'}$=3.0 Hz); mass spectrum, meas. 349.2428, calcd. for C$_{15}$H$_{33}$N$_4$O$_5$ 394.2451.

EXAMPLE 18

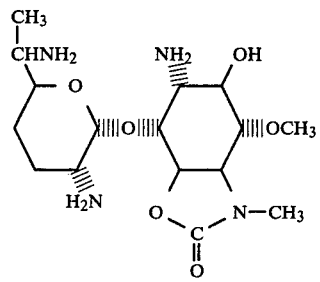

Fortimicin B-4,5-carbamate trihydrochloride

A solution prepared from 0.401 g of 2',6'-di-N-benzyloxycarbonyl-1-azido-1-deaminofortimicin B-4,5-carbamate and 36 ml of 0.2 N hydrochloric acid in methanol is hydrogenated over 0.40 g of 5% palladium on carbon for 4 hours under 3 atmospheres of hydrogen. The catalyst is removed by filtration through a celite mat and the filtrate is evaporated to dryness under reduced pressure to leave a residue. To remove excess hydrochloric acid the residue is repeatedly co-distilled with methanol to give 0.286 g of fortimicin B-4,5-carbamate isolated as the trihydrochloride salt: I.R. (CDCl$_3$) 1742, 1600 and 1495 cm$^{-1}$; P.M.R. (CDCl$_3$) δ 1.84 (d, C$_6$-CH$_3$, J$_{6',7'}$=7.0 Hz), 3.38 (s, C$_4$-NCH$_3$), 4.04 (s, C$_3$-OCH$_3$); mass spectrum meas. 374.2189, calcd. for C$_{16}$H$_{30}$N$_4$O$_6$ 374.2165.

The compounds of this invention are active as systemic antibiotics when injected by parenteral routes of administration, i.e., by the intramuscular, intravenous, intraparitoneal or subcutaneous routes of administration. The compounds can also be administered orally in those instances where it is desirable to sterilize the intestinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 10 to 100 mg/kg of body weight daily are administered to a mammalian patient suffering from an infection caused by susceptible organism.

We claim:

1. A 1,2-di-epi-fortimicin represented by the formula:

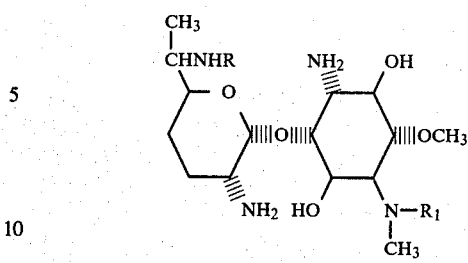

wherein R is hydrogen or lower-alkyl; and $R_1$ is selected from the group consisting of hydrogen, lower-alkyl, aminoloweralkyl, diaminoloweralkyl, N-loweralkylaminoloweralkyl, N,N-diloweralkylaminoloweralkyl, hydroxyloweralkyl, amino hydroxy-loweralkyl, N-loweralkylaminohydroxyloweralkyl, N,N-diloweralkylaminohydroxyloweralkyl, acyl of the formula

wherein $R_2$ is loweralkyl, aminoacyl, hydroxy-substituted aminoacyl, diaminoacyl, hydroxyacyl, hydroxy-substituted diaminoacyl, N-loweralkylaminoacyl, N,N-diloweralkylaminoacyl, hydroxy-substituted-N-loweralkylaminoacyl and hydroxy-substituted-N,N-diloweralkylaminoacyl wherein each acyl is of the formula

$R_2$ being loweralkyl, and the pharmaceutically acceptable salts thereof.

2. A compound of claim 1 wherein R is hydrogen.
3. A compound of claim 1 wherein $R_1$ is hydrogen.
4. A compound of claim 1 wherein $R_1$ is glycyl.
5. A compound of claim 2 wherein $R_1$ is hydrogen: 1,2-di-epi-fortimicin B or a pharmaceutically acceptable salt thereof.
6. A compound of claim 2 wherein $R_1$ is glycyl: 1,2-di-epi-fortimicin A or a pharmaceutically acceptable salt thereof.
7. A compound of claim 2 wherein $R_1$ is sarcosyl: 1,2-di-epi-4-N-sarcosylfortimicin B or a pharmaceutically acceptable salt thereof.
8. A compound of claim 2 wherein $R_1$ is β-alanyl: 1,2-di-epi-4-N-β-alanylfortimicin B or a pharmaceutically acceptable salt thereof.
9. A compound of claim 2 wherein $R_1$ is 2-hydroxy-4-aminobutyl: 1,2-di-epi-4-N-(2-hydroxy-4-aminobutyl)fortimicin B or a pharmaceutically acceptable salt thereof.
10. A compound of claim 2 wherein $R_1$ is 2-hydroxy-4-aminobutyryl: 1,2-di-epi-4-N-(2-hydroxy-4-aminobutyryl) fortimicin B or a pharmaceutically acceptable salt thereof.

* * * * *